United States Patent [19]

Allred, III

[11] Patent Number: 4,854,302

[45] Date of Patent: Aug. 8, 1989

[54] VIDEO EQUIPPED ENDOSCOPE WITH NEEDLE PROBE

[75] Inventor: Jimmie B. Allred, III, Skaneateles, N.Y.

[73] Assignee: Welch Allyn, Inc., Skaneateles Falls, N.Y.

[21] Appl. No.: 119,707

[22] Filed: Nov. 12, 1987

[51] Int. Cl.<sup>4</sup> ............................ A61B 1/00; A61B 1/06
[52] U.S. Cl. .......................................... 128/6; 128/4; 358/98
[58] Field of Search .................... 128/4, 6, 303.15; 358/98; 350/96.26

[56] References Cited

U.S. PATENT DOCUMENTS

| | | | |
|---|---|---|---|
| 4,281,929 | 8/1981 | Lord et al. | 350/96.26 |
| 4,440,157 | 4/1984 | Shishido | 128/6 |
| 4,491,865 | 1/1985 | Danna et al. | 358/98 |
| 4,539,976 | 9/1985 | Sharpe | 128/6 |
| 4,601,284 | 7/1986 | Arakawa et al. | 128/6 |
| 4,607,622 | 8/1986 | Fritch et al. | 128/6 |
| 4,643,546 | 2/1987 | Richards | 351/205 |

FOREIGN PATENT DOCUMENTS

| | | | |
|---|---|---|---|
| 0138607 | 4/1985 | European Pat. Off. | 350/96.26 |
| 1967105 | 2/1977 | Fed. Rep. of Germany | 350/96.26 |
| 0015117 | 1/1986 | Japan | 358/98 |
| 87/02473 | 4/1987 | PCT Int'l Appl. | 350/96.26 |

OTHER PUBLICATIONS

NSG America, Inc. Selfoc Rod Lens (brochure) 1986.

Primary Examiner—Leo P. Picard
Assistant Examiner—Jessica Harrison
Attorney, Agent, or Firm—Wall and Roehrig

[57] ABSTRACT

An instrument for penetrating a small opening for closely examining an interior target. The instrument has a narrow needle probe that forms an image of the target and carries it into a main housing. In the housing, a miniature solid-state imager receives the image and forms a video signal that is transmitted, through a long flexible conduit, to a video monitor. The probe is formed of a steel tubular sleeve containing a self-focusing rod lens. A fiber optic bundle surrounds the rod lens to carry illumination to the end of the sleeve for illuminating the target area. A guide tube can be affixed on the sleeve to guide a tool into the target area.

15 Claims, 2 Drawing Sheets

VIDEO EQUIPPED ENDOSCOPE WITH NEEDLE PROBE

BACKGROUND OF THE INVENTION

This invention relates to a video instrument that is equipped with a needle-like probe capable of being inserted into an extremely small opening to provide a full color video image of an ordinarily inaccessible target and, in particular, to a medical instrument that includes a needle-like probe that can be passed through a small surgical incision to view a specific target inside the body as for example the interior of the eye.

Needle probes have been used in the medical art for some time for viewing interior parts of the body. When using these probes, however, the target can be viewed through an eye piece by only one person. Furthermore, the degree of control over the instrument is extremely limited because the user must maintain his eye aligned at all times with the eye piece. These direct viewing instruments do not lend themselves for use in ophthalmology because of the high risk of the probe contacting delicate parts of the inner eye. Adapting a camera for use in conjunction with a needle probe has also proven to be unsatisfactory because the weight and size of the camera makes control of the probe difficult and poses a certain danger to the patient.

The use of needle probes equipped with coherent fiber bundles as described in U.S. Pat. No. 4,607,622 represent an advancement in the art, however, the resolution of the images produced are not of the highest quality because of the inherent limitations found in fiber bundles.

It is often necessary to perform microsurgery on the human eye, but there has been no high resolution instrument previously proposed which permits a surgical instrument to be safely introduced into the eye for viewing and control of the instrument within the eye. Observation of the delicate surgical maneuvers is carried out by viewing through the eye's crystalline lens. This can be quite difficult in cases where the view is obstructed, i.e. in cataract or glaucoma patients, or where the injured or diseased tissues are disposed well away from the main axis of the eye.

Endoscopes are diagnostic devices which carry a viewing head at the end of an elongated insertion tube. These are widely used for examination of tissues within body cavities such as the colon and esophago-gastric tract. However, because the minimum size of the viewing head is rather large, i.e., on the order of 5 mm or larger in diameter, it has previously been impossible to insert an endoscope type instrument into a small, delicate organ such as the eye.

Various endoscopes are described, for example, in U.S. Pat. Nos. 4,491,865; 4,074,306; and 2,764,149.

OBJECTS AND SUMMARY OF THE INVENTION

It is an object of the invention to provide an instrument which has a narrow probe that can be inserted into a small, opening and produce a high resolution video image of a remote target.

It is another object of the invention to provide such an instrument which is compact and is easily controlled.

It is a further object to provide a video ophthalmoscope instrument which can guide small surgical instruments within its viewing area.

According to one aspect of this invention, a video equipped endoscope having a needle probe is provided for in vivo examination of tissues of the interior of the human body. From a main housing there extends an elongated probe that is insertable through an incision into the target region. The probe comprises means to carry an image from the interior of the body into the housing where it is incident on a solid-state video imager.

The probe is formed of an elongated outer sleeve that has a proximal end that communicates with the housing, and a distal end. Inside the sleeve is a self-focusing rod lens whose distal end is coterminous with the sleeve distal end and whose proximal end extends into the housing. An optical fiber bundle passes through the main housing and through the sleeve around the rod lens, carrying illumination into the target region.

The solid-state imager includes a CCD or similar miniaturized integrated circuit device, and also includes associated focusing optics which are aligned along the optic axis of the rod lens. The imager produces a video output signal that corresponds to the image that is being carried by the rod lens.

Preferably, the probe is sealed so that it can be sterilized.

A flexible conduit has a proximal end and has a distal end connected to the main housing. A video line (e.g., a cable, conductor pair, or optical fiber) is contained in the flexible sheath as is the optical fiber bundle. A connector at the proximal end of the flexible conduit couples the video line to a video display device and also couples the optical fiber bundle to a lamp or other source of illumination.

The housing is preferably about nine millimeters in diameter and seventy-five millimeters in length so as to be conveniently hand-held by a medical practitioner. The probe sleeve is preferably about thirty three millimeters long by about two millimeters or less in diameter. An optional hollow tube or channel can be carried on the probe and annexed onto and parallel to the probe sleeve, and can be employed for insertion and guidance of a fine-wire or flexible surgical instrument into the target region.

The above and many other objects, features, and advantages of this invention will be more fully appreciated from the ensuing description of a preferred embodiment, which should be considered in connection with the accompanying drawings.

DETAILED DESCRIPTION OF THE PREFERRED EMBODIMENT

Figure 1:
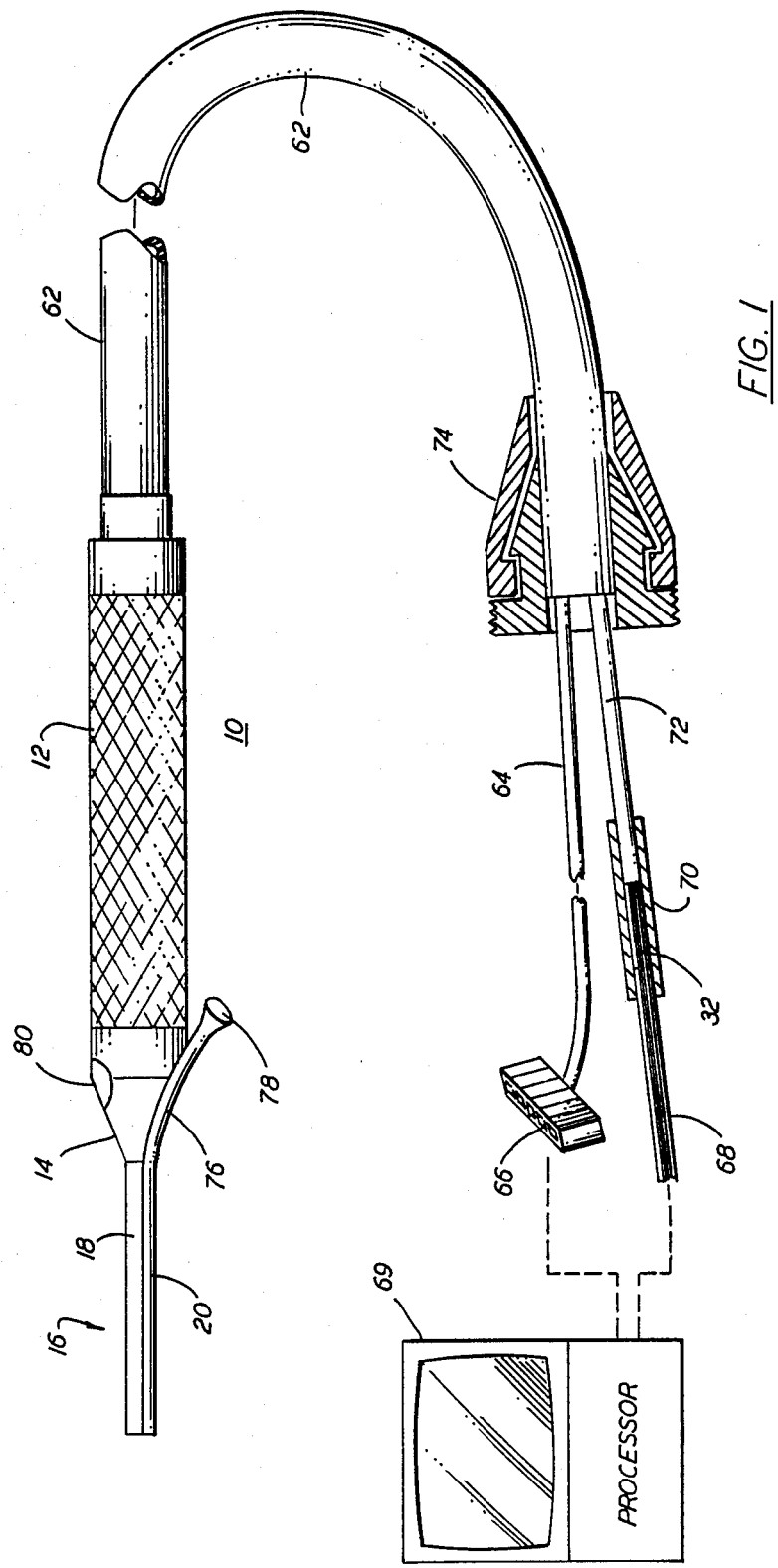
FIG. 1 is a perspective view of the video equipped instrument having a needle probe according to one embodiment of this invention.

With reference initially to FIG. 1 of the drawing, an instrument 10 embodying this invention is formed of a generally cylindrical barrel-type main housing 12 having a tapered or conical distal end 14 onto which an elongated probe 16 is affixed. The probe comprises a cylindrical sleeve or tube 18 of surgical steel. A guide tube 20, which is a surgical steel tube of smaller diameter, is annexed to it, with its distal end coterminous with the forward or distal end of the probe sleeve 18.

Figure 2:
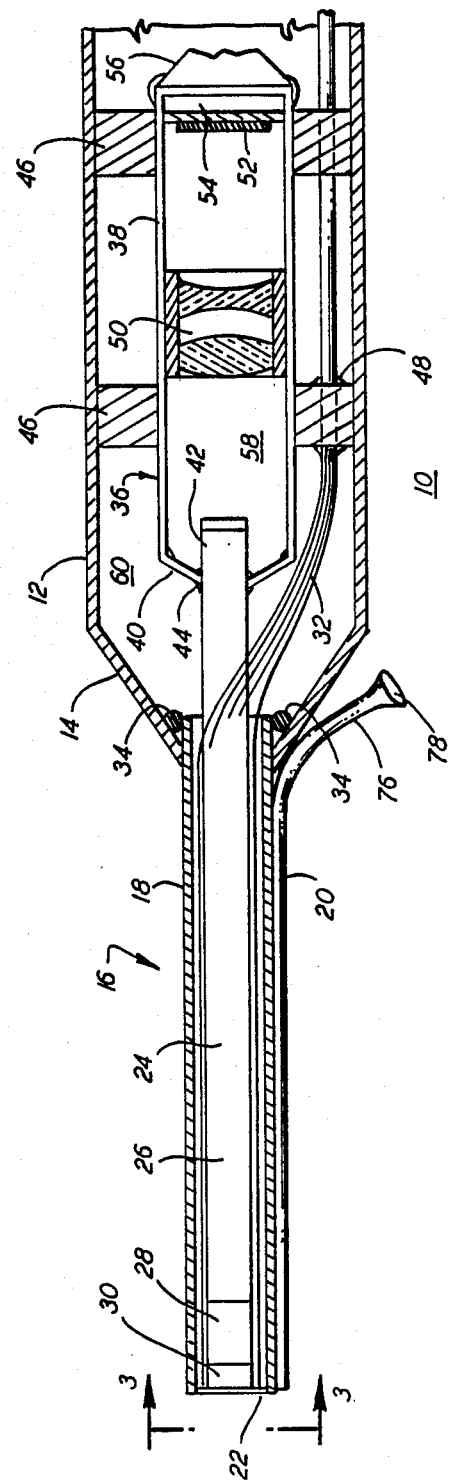
FIG. 2 is a sectional elevation of the probe and housing portions of the embodiment of FIG. 1.
Figure 3:
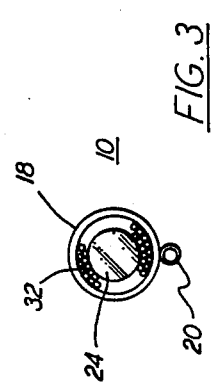
FIG. 3 is a sectional view along the lines 3—3 of FIG. 2.

As better shown in FIGS. 2 and 3, the probe 16 has a glass end cap 22 that hermetically seals the distal end of the sleeve 18. Contained within the sleeve 18 is a self-focusing rod lens 24 that comprises a main rod 26 with an objective lens 28 formed at its distal end, and with an end glass 30 situated in advance of the lens 28. A fiber optic bundle 32 enters the sleeve 18 from within the housing 12, and fans out to surround the rod lens 24. This fiber optic bundle 32 carries light to the forward or distal end of the sleeve for illuminating the interior surfaces of the eye tissue being examined. Sealing means 34, such as epoxy or the like, seals the proximal end of the sleeve 18 to the entrance at the tapered distal end 14 of the housing 12.

The rod lens 24 operates on the principle that its index of refraction N is greatest at the axis, and decreases in proportion to the square of the distance from the axis, so as to be smallest at the edges. The main rod 26 serves as a relay lens and carries an image formed at its distal end back to the end surface at its proximal end. The objective lens 28 acts as a fixed-focus converging lens. In this case, the lens 28 has a viewing angle of between about fifty and sixty degrees. The optical depth of view is between two and twelve millimeters (fixed focus) considered in a saline solution, i.e. a clear fluid isotonic with and having about the same index of refraction as human body fluids such as the aqueous humor of the eye.

Within the main housing 12 is situated an imager assembly 36, which has its optical axis aligned along the optical axis of the rod lens 24. The assembly comprises a tubular enclosure 38 having a front wall 40 which sealably receives the proximal end 42 of the rod lens 24. Epoxy or a similar sealing means 44 hermetically seals the rod lens 24 at the entrance to the wall 40. Support rings 46 support the tubular enclosure 48 within the housing 12 and provide a passageway for the fiber optic bundle 32. An epoxy seal 48 hermetically seals the outer sheath of the fiber optic bundle 32 at the passages through the support rings 46.

About midway within the tabular enclosure 38 are focusing optics 50, which are aligned along the optical axis of the rod lens 24 so as to form an image on a solid state imager 52. The latter is disposed on a printed circuit board 54 at the proximal end of the enclosure 38. An epoxy sealing block 56 seals the proximal end of the enclosure 38 and also encapsulates lines and wires that emanate from the proximal side of the printed circuit board 54. The solid state imager 52 is, for example, a CCD-type integrated circuit having an active area of about 2.5 mm square, i.e. 192 by 165 pixels. An infrared filter may be disposed between the rod lens 24 and the focusing optics 50 of the imager assembly 36.

The tubular enclosure 38 defines an interior space 58 which is preferably nitrogen filled, so as to preclude any problems from condensation or from the presence of possibly corrosive gases. Likewise, the sealed probe 16 and distal part of the housing 12 define a sealed interior space 60 which permits the probe 16 to be sterilized.

Returning now to FIG. 1, at the proximal end of the housing 12 there is connected a flexible sheath or conduit 62 or for example about nine millimeters in diameter by about one hundred eighty centimeters in length. In this conduit is contained video conductor bundle 64 for carrying a video signal from the CCD imager 52 and also containing conductors for providing power, timing signals, and other ancillary signals to the CCD imager 52. The fiber optic cable 32 passes through the housing and also through the conduit 62. The video conductor bundle 64 terminates at its proximal end to a plug-in connector 66 for coupling to a video processor and display unit 69. The proximal end of the optical fiber bundle 32 is highly polished and is contained in a connector ferrule 68 of about one mm equivalent diameter. A soft shrink tube 70 provides strain relief as between the ferrule 68 and a sheath 72 of the bundle 32. The ferrule 68 inserts into a corresponding fitting of an appropriate light source contained within the video processor and display unit.

An end connector 74 of any standard configuration can be employed for mechanically connecting the proximal end of the sheath 62 to the equipment that contains the viewing apparatus.

The proximal section 76 of the guide tube 20 curves out about thirty degrees from the axis of the housing 12 and to the side, i.e., about ninety degrees from the vertical orientation. A flared entrance end 78 facilitates insertion of a fine-wire type of surgical instrument into the insertion tube 20.

A thumb-depression 80 on the top of the distal end wall 14 of the housing 12 serves as an index for maintaining the proper vertical alignment of the CCD imager 52.

The probe sleeve of this embodiment has a length of thirty three millimeters and a diameter of about two millimeters or less in diameter. The main housing 12 is about nine millimeters in diameter and seventy-five millimeters in length. The rod lens 24 has a pupil size of 0.24 mm and its the field of view constitutes about a fifty-five degree circle within an 0.1 by 0.1 inch square.

The guide tube 20, or channel which is optional, is preferably of about 0.8 mm outside diameter, and is soldered to the stainless steel sleeve 18. With the device of this invention, a medical practitioner can perform delicate microsurgery on the interior of the eye wherein the only entrance wound would be the surgical incision of about two to three mm in length. The associated video display device provides an enlarged, erect, full color image of the tissues being examined. A surgical instrument can be guided accurately to an exact location within the eye.

While the invention has been described in detail with reference to a single preferred embodiment, it should be understood that the invention is not limited to that precise embodiment. Rather, many modifications and variations would present themselves to those of skill in the art without departing from the scope and spirit of this invention, as defined in the appended claims.

What is claimed is:

1. A compact needle-probe video endoscopic instrument for examining a remote target area through an opening that includes a main housing;

an elongated probe that is insertable through a very small opening into a target area and including an elongated rigid sleeve that is rigidly attached onto said main housing, and a distal end; optical means contained within said sleeve for carrying an optical image of the target area from the distal end of the sleeve into the interior of the housing, and a fiber optic illumination bundle extending continuously from a remote source of illumination to a distal end of said sleeve for carrying illumination through said sleeve into said target area; a self-contained solid state imager assembly permanently disposed within said main housing and in intimate contact with a proximal end of said optical means, and an imaging element and associated focusing optics along an optic axis of said optical means, arranged for directly focusing the optical image from said optical means onto said imaging element, the latter producing a video output signal corresponding to the image of the target area that is carried by said optical means; coupling means for coupling the video output signal from the imager assembly to a video display device; and means for coupling said fiber optic bundle to said source of illumination and a guide tube affixed onto said sleeve for introducing and guiding a tool into the target area of said probe.

2. The instrument of claim 1 wherein said sleeve is a stainless steel tube substantially 2 mm in diameter or less.

3. The instrument of claim 1 wherein said sleeve includes seal means rendering the probe heat sterilizable.

4. A video needle-probe instrument for viewing the interior of the human eye comprising:
a main housing;
an elongated probe that is insertable through an incision in the eye into the interior thereof and including an elongated outer sleeve having a proximal end this is attached to said housing and a distal end, a self-focusing rod lens in said sleeve having a distal end at the sleeve distal end and a proximal end that extends into the housing and carrying an image of the interior of the eye from its distal end to its proximal end, and an optical fiber bundle passing through the housing and into the sleeve for carrying illumination into the interior of the eye;
a solid state imager assembly permanently within said main housing in intimate contact with the proximal end of said rod lens, and including associated focusing optics along the optic axis of the rod lens, and imaging means for producing a video signal corresponding to the image of the interior of the eye that is carried by said rod lens;
a flexible conduit having a proximal end and a distal end connected to said main housing and containing a video line carrying the video signal from said imager assembly and said fiber optical bundle; and
connector means at the proximal end of said flexible conduit for coupling the video line to a video display device.

5. The instrument of claim 4 wherein said flexible conduit also contains said optical fiber bundle which extends from said probe through said housing and through said conduit to its proximal end, and said connector means includes optical coupling means for coupling the optical fiber bundle to an illumination source.

6. The instrument of claim 4 wherein said rod lens is formed as an elongated cylinder of a material whose index of refraction decreases from its axis outwards.

7. The instrument of claim 4 in which said main housing and said elongated probe include seal means to permit sterilization of the probe.

8. The instrument of claim 4 wherein said imager assembly includes an enclosure mounted within said main housing with a distal end sealably receiving the proximal end of the rod lens, solid-state imager disposed at a proximal end of said enclosure, and said focusing optics disposed about midway between the proximal end of said rod lens and said imaging means.

9. The instrument of claim 4 wherein said probe extends about 33 mm from said housing and has an outside diameter of about 1.8 mm.

10. The instrument of claim 4 wherein said main housing has an outer diameter of about 9 mm.

11. The instrument of claim 4 wherein said probe further comprises a guide tube parallel to and adjacent said probe for passing a tool into the eye.

12. The instrument of claim 11 wherein said guide tube has a distal end coterminous with the distal end of said probe sleeve, and a flared proximal end.

13. The instrument of claim 4 said housing comprising a key on its outer surface to indicate the orientation of the imager assembly.

14. A compact video endoscopic needle-l, robe instrument for viewing the interior of the human eye comprising: a main housing; an elongated probe of a diameter of about 2 mm or less that is insertable through an incision in the eye into the interior thereof and including an elongated outer sleeve having a proximal end that is attached permanently onto said housing and a distal end, a self-focusing rod lens in said sleeve having a distal end at the sleeve distal end and a proximal end that extends into the housing, the rod lens carrying an image of the interior of the eye from its distal end to its proximal end, and an optical fiber bundle passing through the main housing and continuously into the sleeve for carrying illumination into the interior of the eye; a miniature solid state imager assembly permanently disposed within said housing in intimate contact with the proximal end of said rod lens, and including focusing optics along the optic axis of the rod lens and an imaging element for producing a video signal corresponding to the image of the interior of the eye that is carried to it by said rod lens; a flexible conduit having a proximal end and a distal end connected to said main housing and containing a video line carrying the video signal from said imager assembly and said optical fiber bundle; and connector means at the proximal end of said flexible conduit for coupling the video line to a video display device and for coupling said optical fiber bundle to an illumination source.

15. The instrument of claim 14 wherein said sleeve is hermetically sealed to said housing and said housing is hermetically sealed to said flexible conduit, with said imager assembly hermetically sealed within said housing, so that said housing and probe can be sterilized.

* * * * *

UNITED STATES PATENT AND TRADEMARK OFFICE
CERTIFICATE OF CORRECTION

PATENT NO. : 4,854,302

DATED : August 8, 1989

INVENTOR(S) : J.B. Allred, III

It is certified that error appears in the above-identified patent and that said Letters Patent is hereby corrected as shown below:

Col. 6, line 25, please delete "needle-1 robe" and insert --needle probe--.

Signed and Sealed this

Eleventh Day of September, 1990

Attest:

HARRY F. MANBECK, JR.

Attesting Officer      Commissioner of Patents and Trademarks